United States Patent [19]

Mathew

[11] Patent Number: 5,284,975

[45] Date of Patent: Feb. 8, 1994

[54] METHOD OF PREPARING α-D-PHENYLALKYLBENZYL CARBINOL

[75] Inventor: Jacob Mathew, Fenton, Mo.

[73] Assignee: Mallinckrodt Specialty Chemicals Company, Chesterfield, Mo.

[21] Appl. No.: 958,390

[22] Filed: Oct. 8, 1992

[51] Int. Cl.⁵ .......................................... C07C 235/06
[52] U.S. Cl. ................................. 564/171; 564/356; 564/425; 568/807
[58] Field of Search ................. 564/170, 171

[56] References Cited

PUBLICATIONS

G. Frater, *Tetrahedron Letters*, 22: pp. 425–427, 1981.
D. Seebach et al., *Organic Synthesis, Coll. vol. 7*, pp. 153–159. (1990).
B. McEwan, *Propoxyphene Hydrochloride*, pp. 302–317. (1972).
Tetrahedron Letters, vol. 24, No. 47, (1983) pp. 5233–5236.
Tetrahedron Letters, vol. 27, No. 30, (1986) pp. 3511–3514.
Tetrahedron Letters, vol. 28, No. 9 (1987) pp. 985–988.
March, J. *Advanced Organic Chemistry* (1992) John Wiley & Sons, pp. 896–898.

*Primary Examiner*—Glennon H. Hollrah
*Assistant Examiner*—B. M. Burn
*Attorney, Agent, or Firm*—Linda L. Lewis

[57] ABSTRACT

A method of preparing an α-d-phenylalkylbenzyl carbinol by the reaction of a phenylbenzyl ketone with an alkali metal enolate of an amide to form an aldol adduct, which is reduced and purified to form an α-d-phenylalkylbenzyl carbinol, wherein the carbinol so produced possesses analgesic activity. In an embodiment of the invention, a phenylbenzyl ketone is reacted with an alkali metal enolate of an amide to form an aldol adduct, which is reacted with an alkali metal salt of a secondary amine to form a dianion; the dianion is alkylated with an alkyl halide to form an α-isomer of an aldol adduct, which is reduced and purified to form an α-d-phenylalkylbenzyl carbinol possessing analgesic activity.

8 Claims, No Drawings

METHOD OF PREPARING α-D-PHENYLALKYLBENZYL CARBINOL

FIELD OF THE INVENTION

The present invention relates to a method of preparing an α-d-phenylalkylbenzyl carbinol. More specifically, the invention relates to the reaction of a phenylbenzyl ketone with an alkali metal enolate of an amide to form an aldol adduct, which is reduced and purified to form an α-d-phenylalkylbenzyl carbinol. The carbinol so produced possesses analgesic activity.

In an embodiment of the invention, a phenylbenzyl ketone is reacted with an alkali metal enolate of an amide to form an aldol adduct. The aldol adduct is reacted with an alkali metal salt of a secondary amine to form a dianion. The dianion is alkylated with an alkyl halide to form an α-isomer of an aldol adduct, which is reduced and purified to form an α-d-phenylalkylbenzyl carbinol possessing analgesic activity.

BACKGROUND OF THE INVENTION

Certain phenylalkylbenzyl carbinols are known to possess analgesic activity. Specifically, the α,β-(d,1)-(4-dimethylamino-1,2-diphenyl-3-methyl-2-butanol) possesses marked analgesic activity. It has been demonstrated that the analgesic activity resides in the dextrorotatory (α-d) enantiomer. Canadian Patent 1060013 (Gianantonio et al) discloses two methods to prepare the dextrorotatory (α-d) enantiomer of the desired phenylalkylbenzyl carbinols. Gianantonio et al disclose the following two methods:

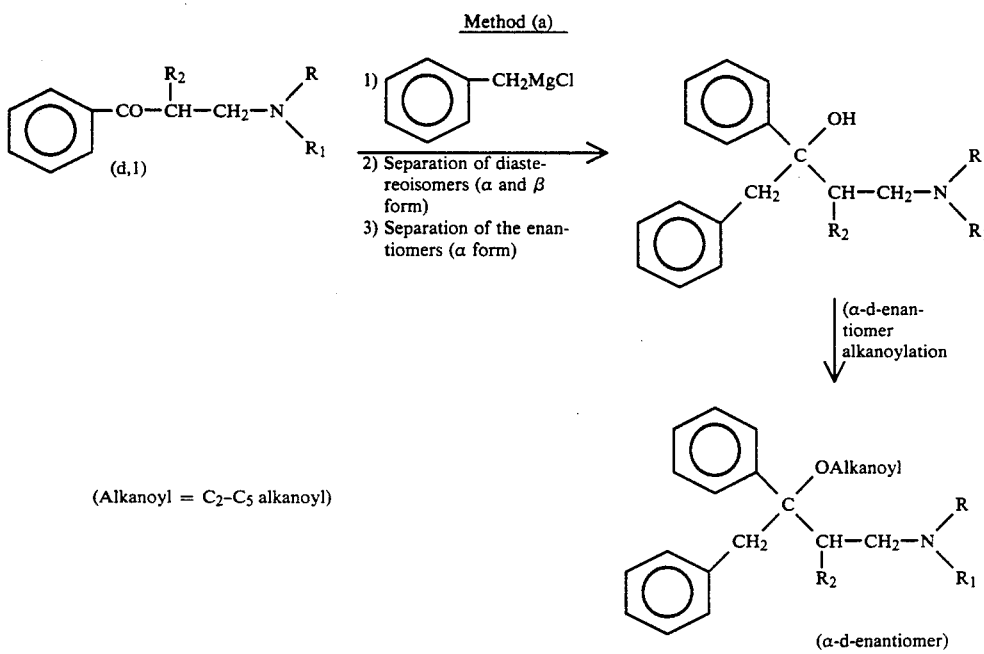

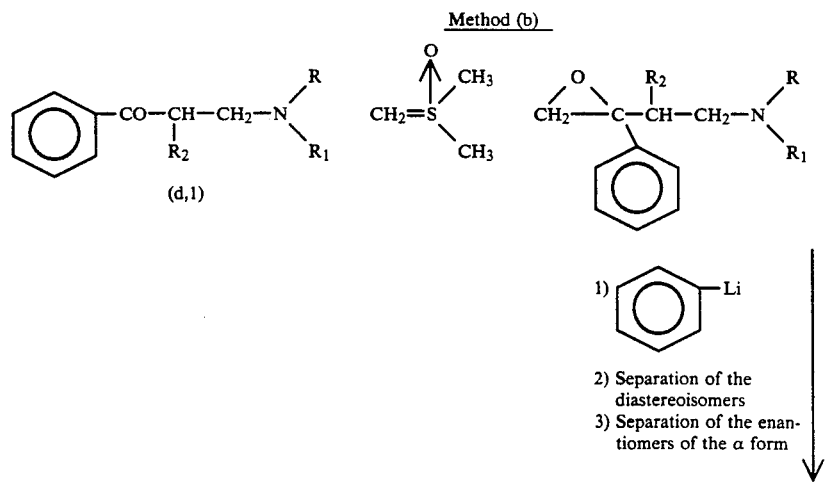

-continued

Method (b)

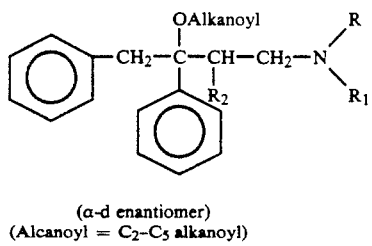

(α-d enantiomer)
(Alcanoyl = $C_2$-$C_5$ alkanoyl)

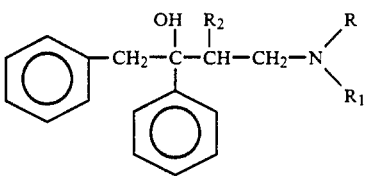

(α-d enantiomer)

According to method (a) the racemic 1-phenyl-2-lower alkyl-3-substituted amino-1-propanone undergoes a Grignard reaction leading predominantly, about 85 to 90%, to the α-diastereoisomer. The mixture is separated into the α and β components by fractional crystallization from aqueous ethanol, the diastereoisomer α being the less soluble component. In accordance with the usual practice the α-diastereoisomer is then resolved into the d and l enantiomers by reaction with an optically active acid to form two diastereoisomeric salts which are in turn readily separable by fractional crystallization. The α-d enantiomer when esterified with an alkyl anhydride, such as propionic anhydride, does not change its configuration.

According to method (b), the α and β components of 1,2-diphenyl-2-hydroxy-3-lower alkyl-4-substituted-aminobutane are obtained by regiospecific opening of the epoxide formed by reaction of (d,l)-1-phenyl-2-lower alkyl-3-substituted amnio-1-propanone and dimethyl sulfoxonium methylide. The separation of the α and β components, the resolution of the a fraction and the esterification of the α-d-enantiomer are carried out following the above procedures.

As can be seen from the above schemes, the β-(d,l)-diastereoisomers and substantial quantities of the α-l-isomer are undesirable by-products whose formation is responsible for the low overall yields of analgesically active substance. The yields of both processes (a) and (b) above range from about 40 to 45%.

The stereoselective α-alkylation of the β-hydroxyester is disclosed by G. Frater, Tetrahedron Letters, 22, 425. The β-hydroxyester is reacted with 2 equivalents of lithium diamine to from the dianion. The dianion is alkylated with an alkylhalide to form the α-alkyl of the β-hydroxyester. The alkylation of β-hydroxyamide is not disclosed, nor the use of such intermediate to prepare an α-d-phenylalkylbenzyl carbinol.

The above methods fail to disclose the present method of preparing an α-d-phenylalkylbenzyl carbinol.

THE PRESENT INVENTION

The present invention relates to a method of preparing an α-d-phenylalkylbenzyl carbinol of the formula,

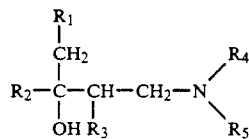     I wherein $R_1$ and $R_2$ are substituted or unsubstituted phenyls; wherein $R_3$, $R_4$ and $R_5$ are lower alkyls of 1 to 4 carbons; and wherein a ketone of the formula

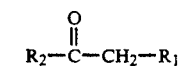     II where $R_1$ and $R_2$ are defined above, is reacted with an alkali metal enolate of an amide of the formula

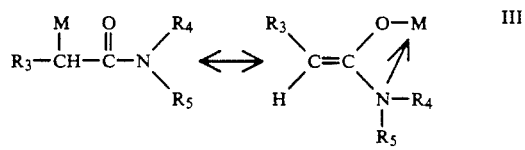     III where $R_3$, $R_4$ and $R_5$ are defined above, and M is an alkali metal, to form an aldol reaction product of the formula

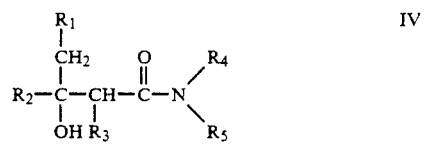     IV

The aldol reaction product (IV) is reduced to form the phenylalkylbenzyl carbinol (I), which is separated into the α and β components and resolved to form the desired α-d-phenylalkylbenzyl carbinol.

In a second method of preparing the α-d-phenylalkylbenzyl carbinol (I) of the present invention, a ketone (II), wherein $R_1$ and $R_2$ are substituted or unsubstituted phenyls; is reacted with the alkali metal enolate of an amide (V), wherein $R_4$ and $R_5$ are lower alkyls of 1 to 4 carbons, to form an aldol reaction product (VI).

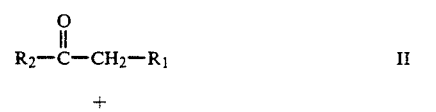     II

+

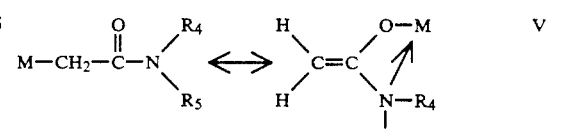     V

↓

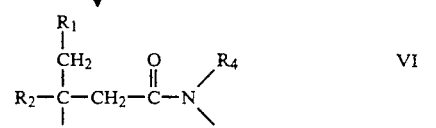     VI

The aldol reaction product is reacted with an alkali metal salt of a secondary amine, M-N(R$_6$)$_2$, wherein R$_6$ is an alkyl of from 1 to 6 carbons, to form the dianion alkali metal salt (VII) of the following formula.

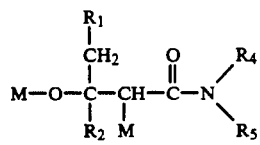  VII

The dianion alkali metal salt is alkylated with an alkylhalide, X-R$_3$, wherein X is a halogen ion, and R$_3$ is an alkyl of from 1 to 4 carbons, to form the α-isomer of the aldol reaction product (IV) of the following formula.

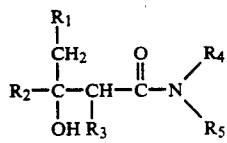  IV

The aldol reaction product is reduced to form the α-isomer of the phenylalkylbenzyl carbinol (I), which is resolved to form the desired α-d-phenylalkylbenzyl carbinol.

DETAILED DESCRIPTION OF THE INVENTION

The ketone starting material (II) of the present invention is a phenylbenzyl ketone wherein the aromatic rings can be substituted with substituents that do not interfere with the aldol reaction to form the adduct, nor the subsequent reduction reaction. Suitable substituents are C$_1$ to C$_4$ lower alkyls, such as methyl, ethyl, propyl and butyl substituents. Examples of suitable starting ketones are phenylbenzyl ketone, p-methylphenylbenzyl ketone, p-isopropylphenylbenzyl ketone, and o,p-dimethyl phenylbenzyl ketone. The preferred ketone is phenylbenzyl ketone.

The amide starting material (III) of the present invention is an enolate, an alkali metal salt of an amide of the formula

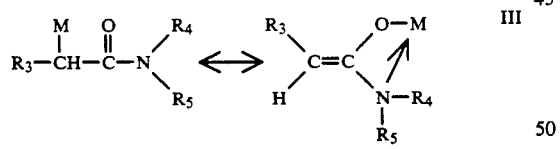  III wherein R$_3$, R$_4$ and R$_5$ are independently lower alkyls of 1 to 4 carbons. Suitable amides include 2-lithium-N,N-dimethylpropionamide, 2-sodium-N,N-diethyl propionamide, 2-lithium-N,N-dipropylbutyramide and 2-sodium-N,N-dimethylpentamide. The preferred amide is 2-lithium-N,N-dimethylpropionamide.

The alkali metal salt of the amide (III) can be prepared as an enolate of the amide by the reaction of the amide with an alkali metal salt of an amine. The amine salt can be prepared from the aklali metal salt of an alkane, such as n-butyllithium or methyllithium, and a secondary amine, such as diisopropyl amine. The reaction to form the amide salt can be performed at a temperature in the range of about 0° C. to about 10° C., to better control the exothermic reaction, and to minimize undesirable side reactions. The preferred reaction temperature is about 0° C. to about 5° C. The reaction can be performed essentially anhydrously, in a polar solvent such a THF or an ether/dioxane mixture. The preferred solvent is THF. Additionally, to prevent undesirable side reactions, the reaction can be performed essentially in the absence of oxygen. This is effected by the use of a nitrogen purge.

To the cooled THF solution containing the alkali metal salt of the amide is added the phenylbenzyl ketone to form the aldol reaction product. Following the reaction, the mixture is quenched using a mineral acid, such as hydrochloric acid or dilute sulfuric acid, with cooling, and the aldol adduct recovered in the organic layer.

The aldol adduct can be reduced using any of the well know methods in the art to reduce amides. Such methods include the use of chemical reducing agents such as lithium aluminum hydride or diborane. The preferred chemical reducing agent is lithium aluminum hydride. The phenylalkylbenzyl carbinol can be recovered by forming the hydrochloric acid salt of the carbinol, which precipitates and is recovered by filtration.

In accordance with the usual practice the α-diastereoisomer is then resolved into the d and l enantiomers by reaction with an optically active acid, such as dibenzoyl-l-tartaric acid, dibenzoyl-d-tartaric acid, l-camphorsulfonic acid or d-camphorsulfonic acid to form two diastereoisomeric salts which are in turn readily separable by fractional crystallization.

In a specific embodiment of the above method of preparing the α-d-phenylalkylbenzyl carbinol, the compound 4-dimethylamino-1,2-diphenyl-3-methyl-2-butanol (XI) is prepared by the reaction of Li-N,N-dimethylpropionamide (VIII) with benzylphenylketone (IX) to form N,N-dimethyl-2-methyl-3,4-diphenyl-3-hydroxybutyramide (X) as follows.

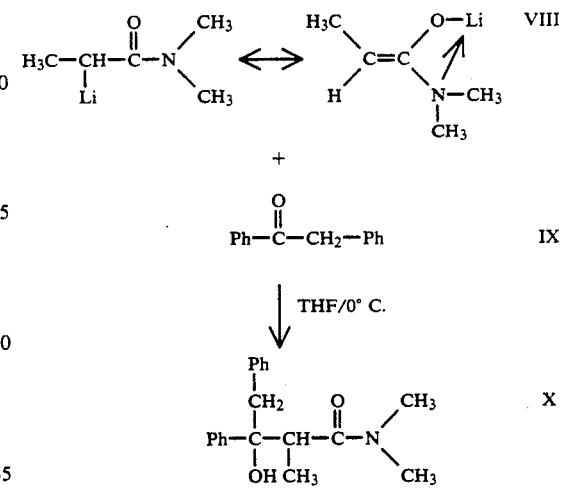

The amide (X) is reduced to form the amine (XI) as follows.

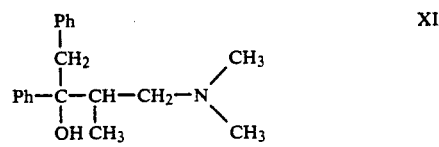  XI

In the second specific embodiment of the invention, a dilithium-alkali metal dianion salt is formed as an intermediate to prepare the α-d-phenylalkylbenzyl carbinol. The suitable amide for the second embodiment is of the formula,

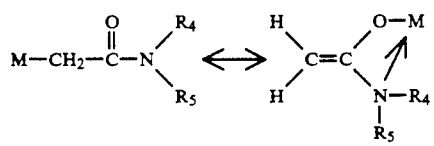

wherein $R_4$ and $R_5$ are defined above. Examples of suitable amides are 2-lithium-N,N-dimethylacetamide and 2-lithium-N,N-diisopropylacetamide. The preferred amide is 2-lithium-N,N-dimethylacetamide.

The compound 4-dimethylamino-1,2-diphenyl-3-methyl-2-butanol (XI) is prepared by the reaction of lithium enolate of N,N-dimethylacetamide (XII) with benzylphenylketone (XIII) to form N,N-dimethyl-3,4-diphenyl-3-hydroxybutyramide (XIV).

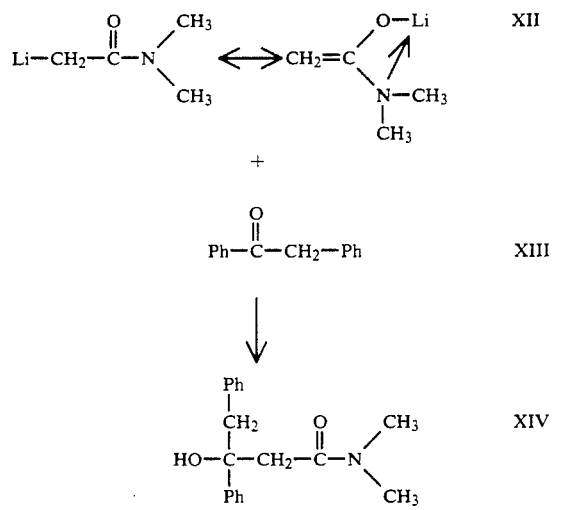

The amide (XIV) is further reacted with lithium-diisopropyl amine (XV) to form the dianion (XVI).

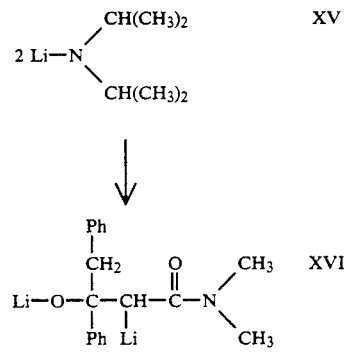

The dianion (XVI) is methylated with a methyl halide, $CH_3X$, (XVII), where X is a halogen ion, such as chloride, bromide or iodide, to yield α-N,N-dimethyl-2-methyl-3,4-diphenyl-3-hydroxybutyramide (X).

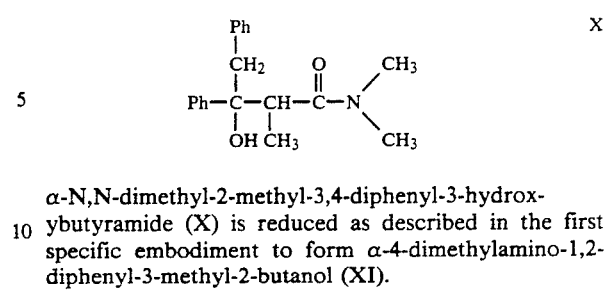

α-N,N-dimethyl-2-methyl-3,4-diphenyl-3-hydroxybutyramide (X) is reduced as described in the first specific embodiment to form α-4-dimethylamino-1,2-diphenyl-3-methyl-2-butanol (XI).

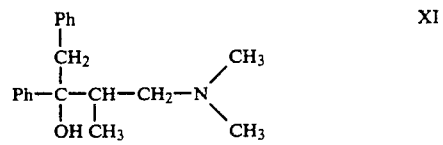

The α-diasterioisomer is resolved as described above to form the α-d-4-dimethylamino-1,2-diphenyl-3-methyl-2butanol.

The following examples are for illustrative purposes only and are not meant to limit the scope of the claims in any way.

EXPERIMENTAL

EXAMPLE 1

Preparation of N,N-dimethyl-2-methyl-3,4-diphenyl-3-hydroxybutyramide, i.e., the Aldol To an ice-cold solution of anhydrous tetrahydrofuran (THF) (100 ml) under a nitrogen purge, is added with stirring, diisopropylamine (10 g, 0.1 mole). To the rapidly stirred solution is added, dropwise, n-butyllithium (2.5 M, 40 ml) over a period of about 15 min. The resulting pale yellow solution is stirred at 0° C. for 30 min to form lithium diisopropylamine. A solution of N,N-dimethylpropionamide (10.2 g, 0.1 mole) in 10 ml THF is added dropwise over a period of about 10 min. The yellow solution containing 2-lithium-N,N-dimethylpropionamide is stirred for about 45 min at 0° C. to complete the reaction. A solution containing benzylphenylketone (18.5 g, 0.09 mole) in THF (20 ml) is added rapidly with stirring, over a period of about 2 to 3 min. The resulting red solution containing the addition product, i.e., N,N-dimethyl-2-methyl-3,4-diphenyl-3-hydroxybutyramide, is stirred for 30 min, then warmed to room temperature, about 25° C. The solution is poured into an solution of 2 N HCl (100 ml) at about 0° C. with rapid stirring to quench the reaction. The temperature of the solution is maintained at 5° C. or less.

The aldol adduct is purified by diluting the solution with ether (100 ml) to form an organic layer and an aqueous layer. The organic layer is recovered and washed twice with 15 ml water and dried over anhydrous magnesium sulfate. The organic layer is filtered and the filtrate recovered. This filtrate is used in the following step.

The aldol can be isolated and purified from the filtrate by evaporation of the solvent, followed by trituration of the yellow solid mass with a hexane and ether (2:1 by volume) solvent to obtain a white powder. The yield of white powder is 22 g, or 83 weight % yield.

Preparation of the Phenyl Benzyl Carbinol, i.e., 4-dimethylamino-1,2-diphenyl-3-methyl-2-butanol by Reduction of the Aldol Adduct The yellow filtrate solution containing the crude aldol is added continuously to an ice cold stirred solution of 1 M LiAlH$_4$ in THF(120 ml) under nitrogen via syringe over a period of about 15 min. The pale yellow frothy mixture is stirred at room temperature (25° C.) for about 6 h to allow the reaction to approach equilibrium. The mixture is quenched by the slow addition of ice-cold water (2.5 ml), 20% by weight NaOH (3 ml) and water (6 ml) to hydrolyse and complex the unreacted LiAlH$_4$. The white granular mixture is filtered and the filtrate washed with water (10 ml) and dried over anhydrous MgSO$_4$ and filtered. The filtrate is cooled with ice and 1 M HCl in ether (85 ml) is added to the stirred solution. The resulting thick precipitate is filtered with suction, washed with ether and dried at 50° C. to obtain 20 g of the HCl salt of the title compound. This salt is used in the following step.

The free base of the salt can be obtained by dissolving the salt in hot water and adjusting the pH to 9 with NH$_4$OH and extracting with ether.

Separation of the α and β Components to Recover α-(d,1)-4-Dimethylamino-1,2-diphenyl-3-methyl-2-butanol The above HCl salt (20 g) is recrystallized by dissolving the salt in boiling methanol (50 ml), cooling with stirring to 50° C., and adding ethyl acetate (20 ml) to precipitate the salt. The mixture is cooled with stirring to 0° C. and kept in the freezer at 0° C. for 4 h. The mixture is filtered and the white powder solids recovered and dried at 50° C. for 1 h. The recrystallization yielded 11 g of solid or 55 wt % yield.

The recovered white powder is dissolved in warm (70° to 80° C.) water (200 ml) and the pH adjusted to 10 with NH$_4$OH. The mixture separates upon standing into an upper oily phase and a lower aqueous phase. The oily phase is extracted with 100 ml ether twice and dried over anhydrous MgSO$_4$. The ether is evaporated to give a viscous oil (9.8 g). This viscous oil is used in the following step.

The oil is analysed by HPLC and found to be >99% α-(d,1)-4-dimethylamino-1,2-diphenyl-3-methyl-2-butanol.

Resolution of d and l Enantiomers by Reaction with an Optically Active Acid to Yield the α-d-4-dimethylamino-1,2-diphenyl-3-methyl-2-butanol The above viscous oil is warmed to 60° to 70° C. with ethanol (80 ml) and d-10-camphorsulfonic acid (9 g) is added to solvate the d form of the α-carbinol. The warm mixture is maintained until a clear solution is obtained. The solution is cooled to 50° C. and then acetone (40 ml) is added to precipitate the l-form of the carbinol. The solution is stirred and cooled to 0° C. in a freezer. The cloudy mixture is maintained at 0° C. for 6 h. The thick white cake is filtered and washed with acetone and ether. The filter cake is air dried to yield 11 g of white powder. The powder is stirred with warm water at 60° C. and adjusted to pH 10 with NH$_4$OH, yielding an oily phase and an aqueous phase. The oily mixture is extracted with hexane and washed with water. The organic extract is dried over anhydrous MgSO$_4$ yielding 6 g of α-d-4-dimethylamino-1,2-diphenyl-3-methyl-2-butanol as a white powder.

EXAMPLE 2

Preparation of α-d-4-dimethylamino-1,2-diphenyl-3-methyl-2-butanol by forming the Dilithium Dianion Salt To a stirred ice-cold (0° C.) solution of 10 g (0.1 mole) diisopropylamine in 100 ml of anhydrous THF under nitrogen gas is added, dropwise, 40 ml (2.5 M) n-butyllithium over a period of about 15 min to form lithium diisopropylamine solution, which is a pale yellow. To the amine solution is added 8.8 g (0.1 mole) N,N-dimethylacetamide in 10 ml THF, dropwise, via syringe, over a period of 10 min. The resulting lithium enolate of N,N-dimethylacetamide solution is deep yellow, and is stirred for 45 min at 0° C. A solution of 18.5 g (0.095 mole) benzylphenylketone in 20 ml of THF is added rapidly over a period of about 2 min to the enolate solution. An orange N,N-dimethyl-3,4-diphenyl-3-hyroxybutyramide solution is formed, and is stirred at 0° C. for about 15 min. Then 40 ml (2.5 M) n-butyllithium is added dropwise via syringe to form a deep red dianion solution. The dianion solution is stirred at about −20° C. for 30 min. Methyl bromide (19 g, 0.2 mole, 2 equivalents) in 20 ml THF is added slowly to methylate the dianion. The resulting N,N-dimethyl-2-methyl-3,4-diphenyl-3-hydroxybutyramide mixture is held at about −20° C. for about 1 h, and a cloudy yellow suspension is formed. The suspension is warmed to room temperature (25° C.), then quenched with 200 ml of a 0° C. solution of 2 N HCl, which is added with rapid stirring. The quenched, pale yellow solution is diluted with 200 ml ether. The organic layer is recovered and washed with brine and dried over anhydrous MgSO$_4$. The mixture is filtered, yielding a pale yellow solution of N,N-dimethyl-2-methyl-3,4-diphenyl-3-hydroxybutyramide, which is reduced in the following step.

The pure N,N-dimethyl-2-methyl-3,4-diphenyl-3-hydroxybutyramide can be isolated if desired by evaporating the solvent and trituration of the residue with hexane and ether (2:1 by volume) solvent to obtain a white powder (isolated yield, 22 g, 83%). Proton NMR and HPLC indicate this to be exclusively the α-isomer.

The pale yellow solution of N,N-dimethyl-2-methyl-3,4-diphenyl-3-hydroxybutyramide is reduced as described in Example 1, above, to form the α-4-dimethylamino-1,2-diphenyl-3-methyl-2-butanol, 90% in isolated yield. HPLC indicates it is >99% the α isomer. The d and l enantiomers are resolved as described in Example 1 to obtain the α-d-4-dimethylamino-1,2-diphenyl-3-methyl-2-butanol in 34% yield, overall.

I claim:

1. A method of preparing an aldol reaction product of the formula,

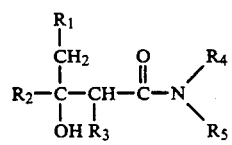

wherein R$_1$ and R$_2$ are independently unsubstituted phenyls or phenyls substituted with C$_1$ and C$_4$ lower alkyls, and R$_3$, R$_4$ and R$_5$ are independently lower alkyls of 1 to 4 carbons; comprising reacting a ketone of the formula,

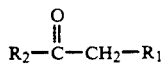

with an alkali metal enolate of an amide of the formula,

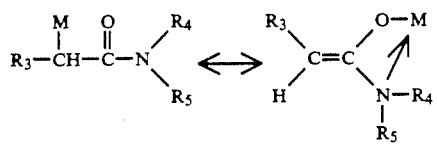

and M is an alkali metal, to to form the aldol reaction product.

2. The method of claim 1 wherein the ketone is selected from the group consisting of phenylbenzyl ketone, p-methylphenylbenzyl ketone, p-isopropylphenylbenzyl ketone, and o,p-dimethylphenylbenzyl ketone.

3. The method of claim 1 wherein the alkali metal enolate of the amide is selected from the group consisting of 2-lithium-N,N-dimethyl propionamide, 2-sodium-N,N-diethyl propionamide, 2-lithium-dipropyl butyramide and 2-sodium-N,N-dimethylpentamide.

4. A method of preparing an a-isomer of an aldol reaction product of the formula,

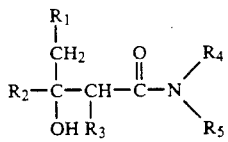

wherein $R_1$ and $R_2$ are independently unsubstituted phenyls or phenyls substituted with $C_1$ and $C_4$ lower alkyls; $R_3$, $R_4$ and $R_5$ are lower alkyls of 1 to 4 carbons; comprising reacting a ketone of the formula,

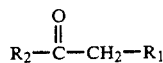

with an alkali metal enolate of an amide of the formula,

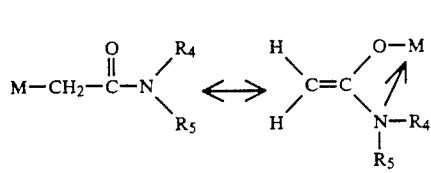

wherein M is an alkali metal, to form an aldol reaction product of the formula,

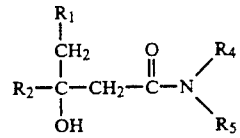

wherein the aldol reaction product is reacted with an alkali metal salt of a secondary amine, $M-N(R_6)_2$, wherein $R_6$ is an alkyl of from 1 to 6 carbons, to form a dianion alkali metal salt of the formula,

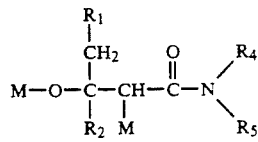

wherein the dianion alkali metal salt is reacted with an alkylhalide, $X-R_3$, wherein X is a halogen ion and $R_3$ is defined above, to form the a-isomer of the aldol reaction product.

5. The method of claim 4 wherein the ketone is selected from the group consisting of phenylbenzyl ketone, p-methylphenylbenzyl ketone, p-isopropylphenylbenzyl ketone, and o,p-dimethylphenylbenzyl ketone.

6. The method of claim 4 wherein the alkali metal enolate of the amide is selected from the group consisting of 2-lithium-N,N-dimethylacetamide and 2-lithium-N,N-diisopropyl acetamide.

7. A method of preparing N,N-dimethyl-2-methyl-3,4-diphenyl-3-hydroxybutyramide comprising reacting lithium-N,N-dimethylpropionamide with benzylphenylketone to form the N,N-dimethyl-2-methyl-3,4-diphenyl-3-hydroxybutyramide.

8. A method of preparing the α-isomer of N,N-dimethyl-2methyl-3,4-diphenyl-3-hydroxybutyramide comprising reacting lithium-N,N-dimethylacetamide with benzylphenylketone to form the N,N-dimethyl-3,4-diphenyl-3-hydroxybutyramide;
wherein the amide is further reacted with lithium diisopropyl amine to form a dianion; and
wherein the dianion is methylated with a methyl halide to form the α-isomer of N,N-dimethyl-2-methyl-3,4-diphenyl-3-hydroxybutyramide.

* * * * *